(12) United States Patent
Tsuchiya et al.

(10) Patent No.: US 6,206,671 B1
(45) Date of Patent: Mar. 27, 2001

(54) PRESSURE MOLDING APPARATUS

(75) Inventors: Masatoshi Tsuchiya; Atsushi Mogami; Yutaka Kobayashi, all of Tokyo; Hideki Ohno; Masato Sekino, both of Tokuyama, all of (JP)

(73) Assignees: Tokuyama Corporation; Yamato Scientific Co, LTD, both of (JP)

( * ) Notice: Subject to any disclaimer, the term of this patent is extended or adjusted under 35 U.S.C. 154(b) by 0 days.

(21) Appl. No.: 09/243,420

(22) Filed: Feb. 3, 1999

(30) Foreign Application Priority Data

Feb. 10, 1998 (JP) .................................................. 10-028582

(51) Int. Cl.[7] ............................. A61C 13/00; B29C 45/53
(52) U.S. Cl. ............................. 425/145; 264/19; 425/193
(58) Field of Search .................................... 425/145, 149, 425/178, 190, 193, 547, 567, 544; 264/16, 19, 328.13, 645, 328.5

(56) References Cited

U.S. PATENT DOCUMENTS

| | | | |
|---|---|---|---|
| 4,880,373 | * 11/1989 | Balog et al. | 425/149 |
| 5,049,054 | * 9/1991 | Schaidl et al. | 425/78 |
| 5,121,406 | * 6/1992 | Hugo et al. | 373/142 |
| 5,302,104 | * 4/1994 | Ueda | 425/178 |
| 5,474,733 | * 12/1995 | Koide et al. | 264/328.1 |
| 5,603,305 | * 2/1997 | Miyake et al. | 123/568 |
| 5,897,885 | * 4/1999 | Petticrew | 425/178 |

* cited by examiner

Primary Examiner—Harold Pyon
Assistant Examiner—Emmanuel Luk
(74) Attorney, Agent, or Firm—Smith, Gambrell & Russell, LLP

(57) ABSTRACT

A pressure molding apparatus comprises a furnace defining a heating space for accommodating a mold assembly including a mold body charged with a raw material to be molded, and a pressure piston for pressurizing the raw material; heating means for heating the heating space; and load imposing means for imposing a load on the pressure piston to mold the raw material. The load imposing means includes at least one weight means and weight supporting means. The weight supporting means is selectively set in a load-free state in which the weight supporting means supports the weight means so that the weight of the weight means is not imposed on the pressure piston, and a load imposed state in which the weight supporting means releases the support of the weight means so that the weight of the weight means is imposed on the pressure piston.

6 Claims, 8 Drawing Sheets

(a)

(b)

PRESSURE MOLDING APPARATUS

FIELD OF THE INVENTION

This invention relates to, but is not restricted to, a pressure molding apparatus suitable for forming a dental crown by heating and pressurizing a ceramic raw material, such as glass-ceramics.

DESCRIPTION OF THE PRIOR ART

As is well known among people skilled in the art, a mold assembly composed of a mold body and a pressure piston is used to mold a ceramic raw material, such as glass-ceramics, into a dental crown. In the mold body, a molding cavity, a raw material charging cavity, and a sprue are formed. The raw material charging cavity is open upwards, and the sprue extends downward from the raw material charging cavity to the molding cavity. The raw material charging cavity of the mold body is charged with a raw material to be molded, i.e., a ceramic material such as glass-ceramics. Then, a lower portion of the pressure piston is inserted into the raw material charging cavity. An upper portion of the pressure piston protrudes upward from the mold body. Then, the mold assembly is accommodated into a heating space of a furnace in a pressure molding apparatus to heat the raw material to a suitable temperature. At the same time, a load is imposed on the pressure piston to pressurize the raw material. As a result, the raw material charged into the raw material charging cavity is flowed into the molding cavity through the sprue to mold it into a required form. Usually, the amount of the raw material charged is larger than the capacity of the molding cavity. Thus, the resulting dental crown is accompanied by an additional portion located in the sprue and the raw material charging cavity of the mold body. Such an additional portion is later removed from the dental crown by machining. Imposition of the load on the pressure piston is performed by a pneumatic cylinder mechanism.

The ceramic softened by heating has a relatively high viscosity of, say, about $10^4$ to $10^6$ poises. Such a raw material needs to be flowed, as required, against resistance due to the escape of air from the molding cavity (the mold body is usually formed of a porous material, and air in the molding cavity escapes through the mold body itself). For this purpose, it is necessary to apply a pressure of, say, about 5 $kg/cm^2$ to the pressure piston. To impose a load on the pressure piston fully stably, a considerably large, high performance pneumatic cylinder mechanism is needed. Hence, a molding apparatus has to be considerably bulky and expensive. The use of a relatively small, low performance pneumatic piston mechanism may often result in a stick-slip phenomenon (a phenomenon in which when the load is imposed on the pressure piston to flow the raw material, descent of the pressure piston is stopped accidentally, thereby terminating the flow of the raw material). The stick-slip phenomenon would make the raw material flow into the molding cavity insufficient and form flow mark on the molded dental crown.

SUMMARY OF THE INVENTION

A main object of the present invention is to provide a novel and improved pressure molding apparatus which does not require a large, expensive pneumatic cylinder mechanism, can thus be produced in a small size and at a low cost, and nonetheless can impose a completely stable load on a pressure piston.

Another object of the invention is to provide a novel and improved pressure molding apparatus which can bring a mold assembly to a required position fully easily, when accommodating the mold assembly into a heating space of a furnace.

The inventors of the present invention have conducted in-depth studies, and found that the main object can be attained by selectively applying the weight of weight means to a pressure piston, instead of using a pneumatic cylinder mechanism.

That is, the present invention provides, as a pressure molding apparatus for attaining the main object, a pressure molding apparatus comprising:

a furnace defining a heating space for accommodating a mold assembly including a mold body charged with a raw material to be molded, and a pressure piston for pressurizing the raw material;

heating means for heating the heating space; and load imposing means for imposing a load on the pressure piston to mold the raw material, wherein the load imposing means includes at least one weight means and weight supporting means, and the weight supporting means is selectively set in a load-free state in which the weight supporting means supports the weight means so that the weight of the weight means is not imposed on the pressure piston, and a load imposed state in which the weight supporting means releases the support of the weight means so that the weight of the weight means is imposed on the pressure piston.

Preferably, the load imposing means includes first weight means and second weight means, and the weight supporting means is selectively set in the load-free state in which the weight supporting means supports both the first weight means and the second weight means so that none of the weights of the first weight means and the second weight means are imposed on the pressure piston, a low load imposed state in which the weight supporting means releases the support of the first weight means so that the weight of the first weight means is imposed on the pressure piston, and a high load imposed state in which the weight supporting means releases the support of both the first weight means and the second weight means so that the weights of the first and second weight means are imposed on the pressure piston. Preferred embodiments are as follows: The furnace has a floor wall defining a lower surface of the heating space, and a ceiling wall defining an upper surface of the heating space; the mold assembly is laid on the floor wall; the pressure piston is stretched outward upwardly from the mold body; the first weight means is placed above the pressure piston and stretched through the ceiling wall; the second weight means is placed above the first weight means; the weight supporting means includes a supporting member, and hoisting and lowering means for hoisting and lowering the supporting member; when the supporting member is brought to a hoisted position, the second weight means supports the first weight means, and the supporting member supports the second weight means, and supports the first weight means via the second weight means; when the supporting member is lowered beyond a low load imposed position, the first weight means contacts the pressure piston, so that the support of the first weight means by the second weight means is released, whereby the load of the first weight means is imposed on the pressure piston; when the supporting member is further lowered beyond a high load imposed position, the second weight means contacts the first weight means, so that the support of the second weight means by the supporting member is released, whereby the load of the first weight means is imposed on the pressure piston, and the load of the second weight means is also imposed on the pressure piston via the first weight means. The second weight means includes a bracket member having an opening formed in a bottom wall; the first weight means includes a rod extending in an up-and-down direction through the opening; an engagingly stopping flange positioned above the bottom wall of the bracket member, and a contact flange positioned below the bottom wall of the bracket member are disposed on the rod; the bottom wall of the bracket member supports the engagingly stopping flange, whereby the second weight means supports the first weight means; and the bottom wall of the bracket member contacts the contact flange, whereby the load of the second weight means is imposed on the pressure piston via the first weight means. A contact member is disposed on the bracket member, and the supporting member supports the second weight means by contacting a lower surface of the contact member. In an embodiment for attaining the other object, the furnace includes a floor wall defining a lower surface of the heating space, and a furnace floor plate removably mounted on the floor wall, and position regulating means for regulating the position of the mold assembly to be placed on an upper surface of the furnace floor plate is disposed on the upper surface of the furnace floor plate.

DETAILED DESCRIPTION OF THE PREFERRED EMBODIMENTS

The present invention will now be described in more detail by reference to the accompanying drawings which show preferred embodiments of a pressure molding apparatus constructed in accordance with the present invention.

Figure 1:
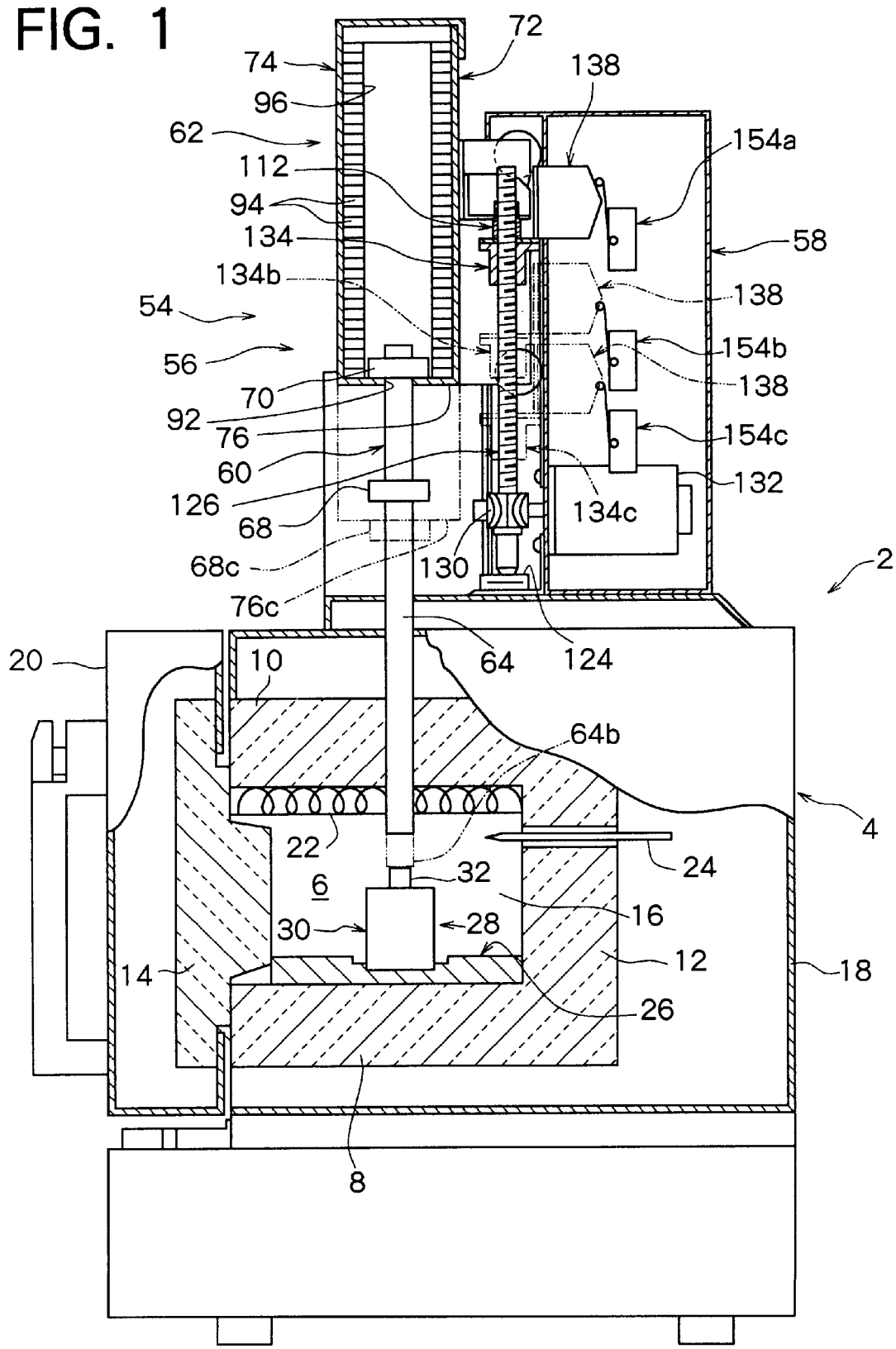
FIG. 1 is a side view, partly in cross section, of a preferred embodiment of a pressure molding apparatus constructed in accordance with the present invention.

With reference to FIG. 1, a pressure molding apparatus shown entirely by the numeral 2 has a heating furnace 4. This heating furnace 4 has a heating space 6 which may be in a nearly rectangular parallelopipedal shape. The heating space 6 is demarcated by a floor wall 8, a ceiling wall 10, and four side walls, i.e., a rear wall 12, a front wall 14, and both lateral walls 16 (FIG. 1 shows only one of the lateral walls 16). The floor wall 8, ceiling wall 10, rear wall 12, front wall 14, and lateral walls 16 that define the heating space 6 are formed of a refractory material such as firebrick. The floor wall 8, ceiling wall 10, rear wall 12, and lateral walls 16 are held by suitable holding means (not shown) at required positions inside a housing 18 which is in the shape of a box with an open front surface. On the front surface of the housing 18, a door 20 is mounted which is turned about a turn axis extending along an edge thereof, whereby the door 20 is brought to a closing position for closing the front surface of the housing 18 and an opening position for opening the front surface of the housing 18. The front wall 14 is held at an inner surface of the door 20. Thus, when the door 20 is brought to the closing position, the heating space 6 is closed. When the door 20 is brought to the opening position, the front surface of the heating space 6 is opened, so that the interior of the heating space 6 can be accessed. On the ceiling wall 10, heating means 22, which may be an electric resistance heater, is disposed. By this heating means 22, the interior of the heating space 6 is heated to a suitable temperature. Through the rear wall 12, a temperature sensor 24 is disposed. By this temperature sensor 24, the temperature inside the heating space 6 is detected. Based on the temperature detected, energization and deenergization of the heating means 22 are controlled.

Figure 2:
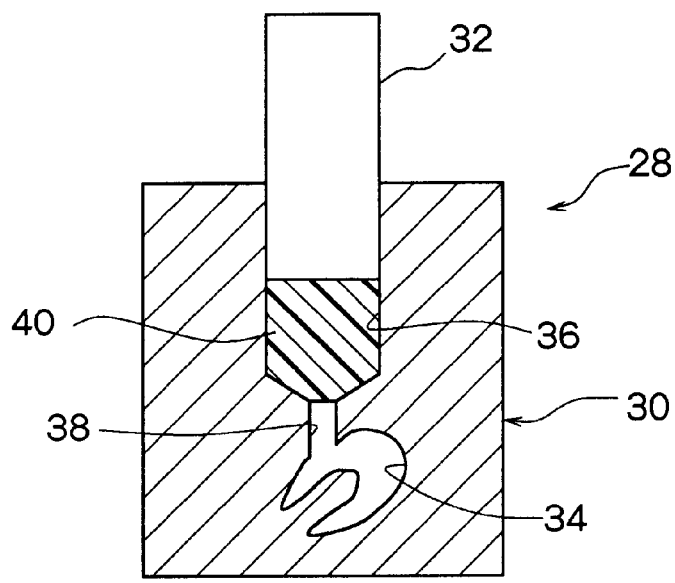
FIGS. 2(a) and 2(b) are sectional views of a mold assembly for use in the pressure molding apparatus of FIG. 1, shown in a state before pressure molding and a state after pressure molding, respectively.
Figure 2:
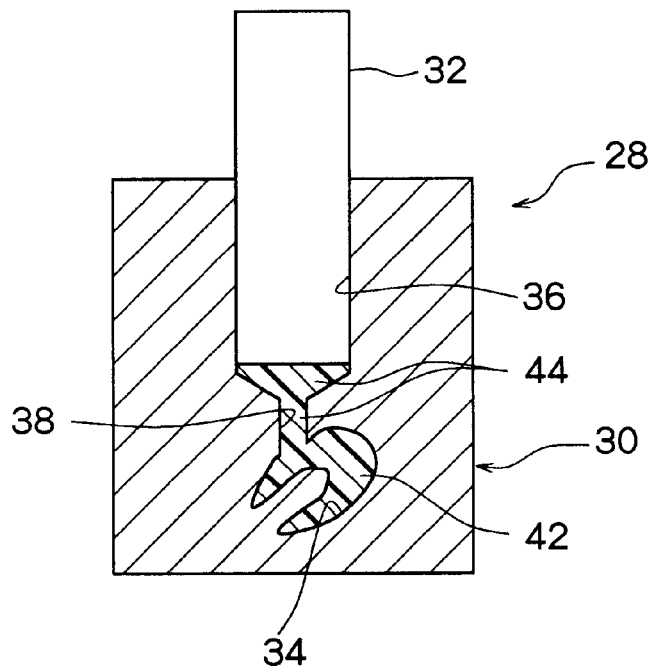

On the floor wall 8, a furnace floor plate 26 which may be formed of a suitable refractory material is laid. The contour of the furnace floor plate 26 may be substantially the same as the cross sectional shape of the heating space 6. The furnace floor plate 26 is laid on the floor wall 8, with its rear edge and lateral edges being contiguous to or close to the rear wall 12 and the lateral walls 16, respectively. On the furnace floor plate 26, a mold assembly entirely indicated at 28 is laid. With reference to FIG. 2(a), the mold assembly 28 is constituted of a mold body 30 and a pressure piston 32. The mold body 30, advantageously formed of a refractory porous material, is in a generally cylindrical shape, and has a molding cavity 34, a raw material charging cavity 36, and a sprue 38. The molding cavity 34 corresponds to the shape of a product to be molded, e.g., a dental crown. The raw material charging cavity 36 has substantially the same sectional shape, e.g., a circular sectional shape, except its lower end portion, and its upper end is open. The sprue 38 extends from the raw material charging cavity 36 to the molding cavity 34. Such mold body 30 can be formed, for example, by forming wax pattern of which shapes correspond to the molding cavity 34, the raw material charging cavity 36 and the sprue 38, fixing the wax pattern in the casting ring using a crucible former, placing an investment (e.g. gypsum) around the wax pattern, setting the investment, and then burning the wax pattern away. The raw material charging cavity 36 of the mold body 30 is charged with a raw material 40 to be molded, which may be a ceramic material such as glass-ceramics. The pressure piston 32 is in the shape of a cylinder having a sectional shape corresponding to the sectional shape of the raw material charging cavity 36. A lower part of the pressure piston 32 is inserted into the raw material charging cavity 36, while an upper part thereof is protruded upward from the mold body 30. As will be further mentioned later, the mold assembly 28 is laid on the furnace floor plate 26, and accommodated in the heating space 6. There, the mold assembly 28 is heated to a suitable temperature, and a load is imposed on the pressure piston 32. Thus, as shown in FIG. 2(b), the raw material 40 to be molded is softened and pressurized, and then flowed through the sprue 38 into the molding cavity 34 to form a dental crown 42. The amount of the raw material 40 charged into the raw material charging cavity 36 for molding is larger than the capacity of the molding cavity 34. Hence, the dental crown 42 involves an additional portion 44. Such an additional portion 44 can be removed mechanically from the dental crown 42 after removing the mold body 30 and withdrawing the dental crown 42 together with the additional portion 44.

Figure 3:
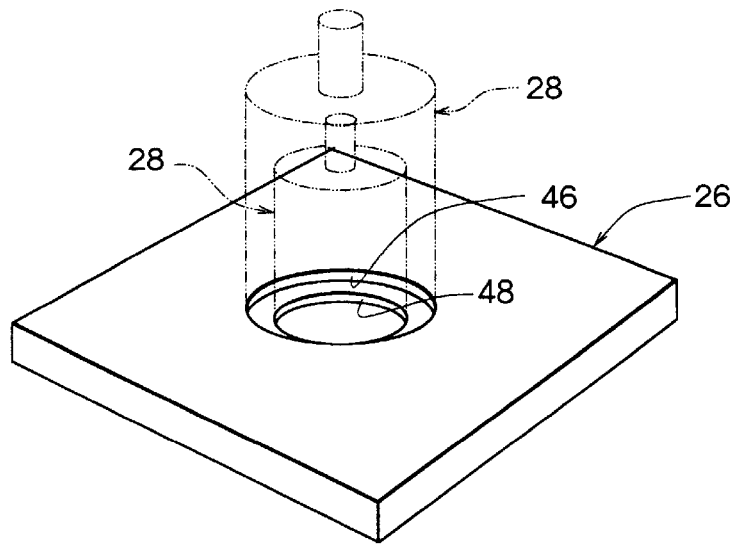
FIG. 3 is a perspective view showing a furnace floor plate for use in the pressure molding apparatus of FIG. 1.
Figure 4:
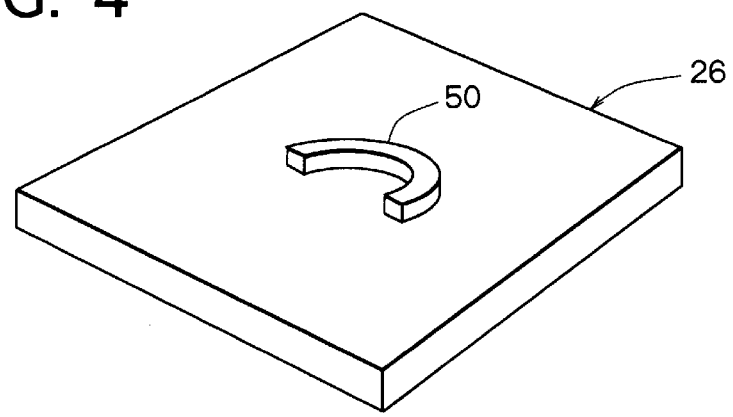
FIG. 4 is a perspective view showing a modification of the furnace floor plate.
Figure 5:
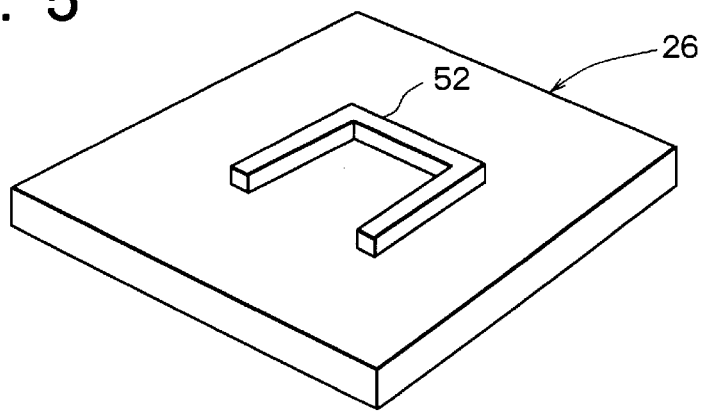
FIG. 5 is a perspective view showing another modification of the furnace floor plate.

Further referring to FIG. 3 along with FIGS. 1 and 2(a), a relatively large diameter circular concave portion 46, and a relatively small diameter circular concave portion 48 placed concentrically at a bottom surface of the circular concave portion 46 are formed at an upper surface of the furnace floor plate 26. The circular concave portions 46 and 48 constitute position regulating means for regulating the position of the mold assembly 28. As shown by a two-dot chain line in FIG. 3, when there is used the mold assembly 28 having a relatively large mold body 30 having an outer diameter corresponding to an inner diameter of the circular concave portion 46, a lower end portion of the mold body 30 is inserted into the circular concave portion 46. Thus, the mold assembly 28 is located at a required position in the heating space 6. When there is used the mold assembly 28 having a relatively small mold body 30 having an outer diameter corresponding to an inner diameter of the circular concave portion 48, a lower end portion of the mold body 30 is inserted into the circular concave portion 48. Thus, the mold assembly 28 is located at a required position in the heating space 6. Instead of forming a concave portion at the upper surface of the furnace floor plate 26, it is possible to form a protrusion of a suitable shape, thereby regulating the position of the mold assembly 28. As illustrated in FIG. 4, for example, an arcuate protrusion 50 having an inner diameter corresponding to the outer diameter of the mold body 30 may be formed at the upper surface of the furnace floor plate 26, and an outer peripheral surface of the lower end portion of the mold body 30 can be brought into contact with the protrusion 50. When the mold body 30 is in a prismatic shape, a channel-like protrusion 52 corresponding to the contour of the mold body 30 may be formed on the furnace floor plate 26, and the lower end portion of the mold body 30 can be positioned inwardly of the protrusion 52.

As shown in FIG. 1, load imposing means indicated generally at the numeral 54 is disposed on an upper surface of the housing 18. This load imposing means 54 is composed of weight means 56 and weight supporting means 58. In the illustrated embodiment, the weight means 56 is composed of first weight means 60 and second weight means 62.

Figure 6:
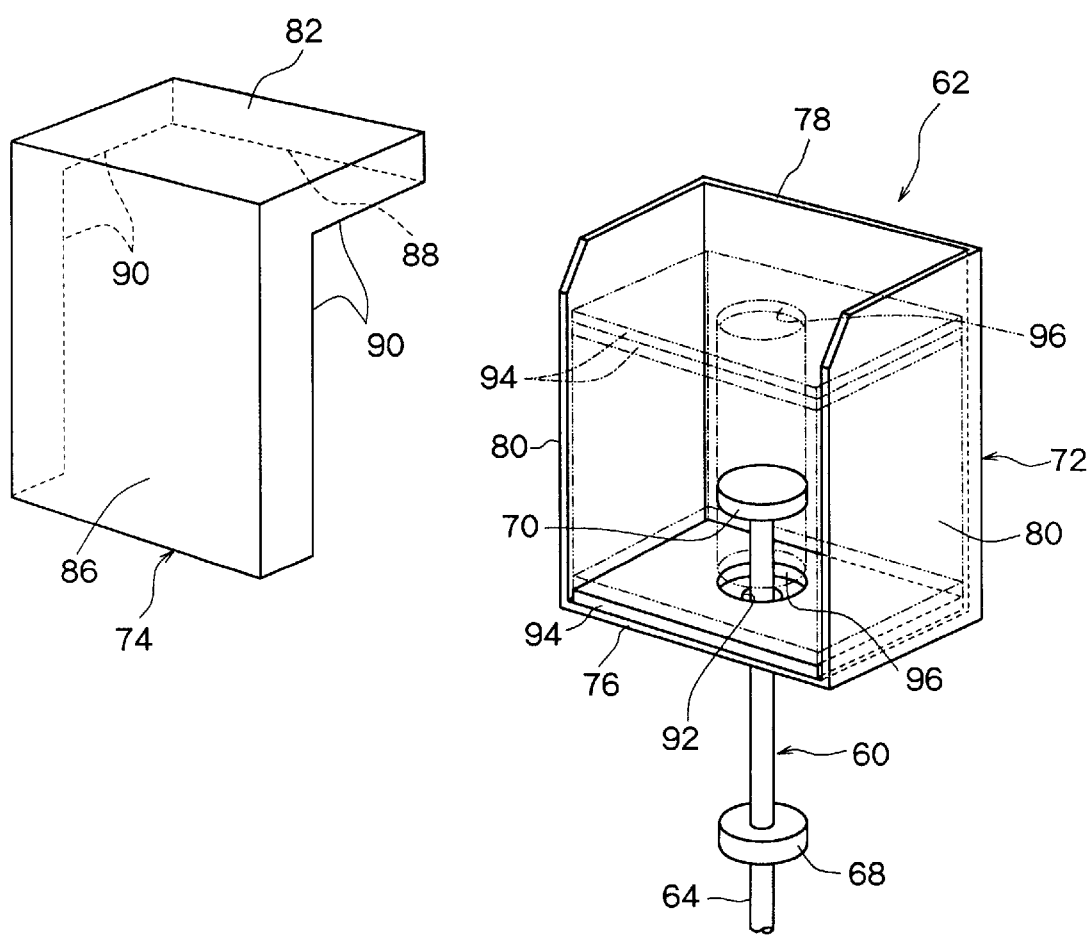
FIG. 6 is an exploded perspective view showing first weight means and second weight means in the pressure molding apparatus of FIG. 1.

With reference to FIG. 6 along with FIG. 1, the first weight means 60 is formed from a slender rod 64 extending through the ceiling wall 10 of the aforementioned heating furnace 4 and the housing 18. The rod 64 which may be formed of a suitable refractory material has a circular sectional shape, and is disposed so as to be movable upward and downward relative to the heating furnace 4. As will be easily understood by reference to FIG. 1, the rod 64 is matched to the pressure piston 32 of the mold assembly 28 placed in the heating space 6 of the heating furnace 4. To a nearly middle portion, and an upper end portion of the rod 64, circular flanges 68 and 70, respectively, are fixed by suitable means such as welding.

Figure 7:
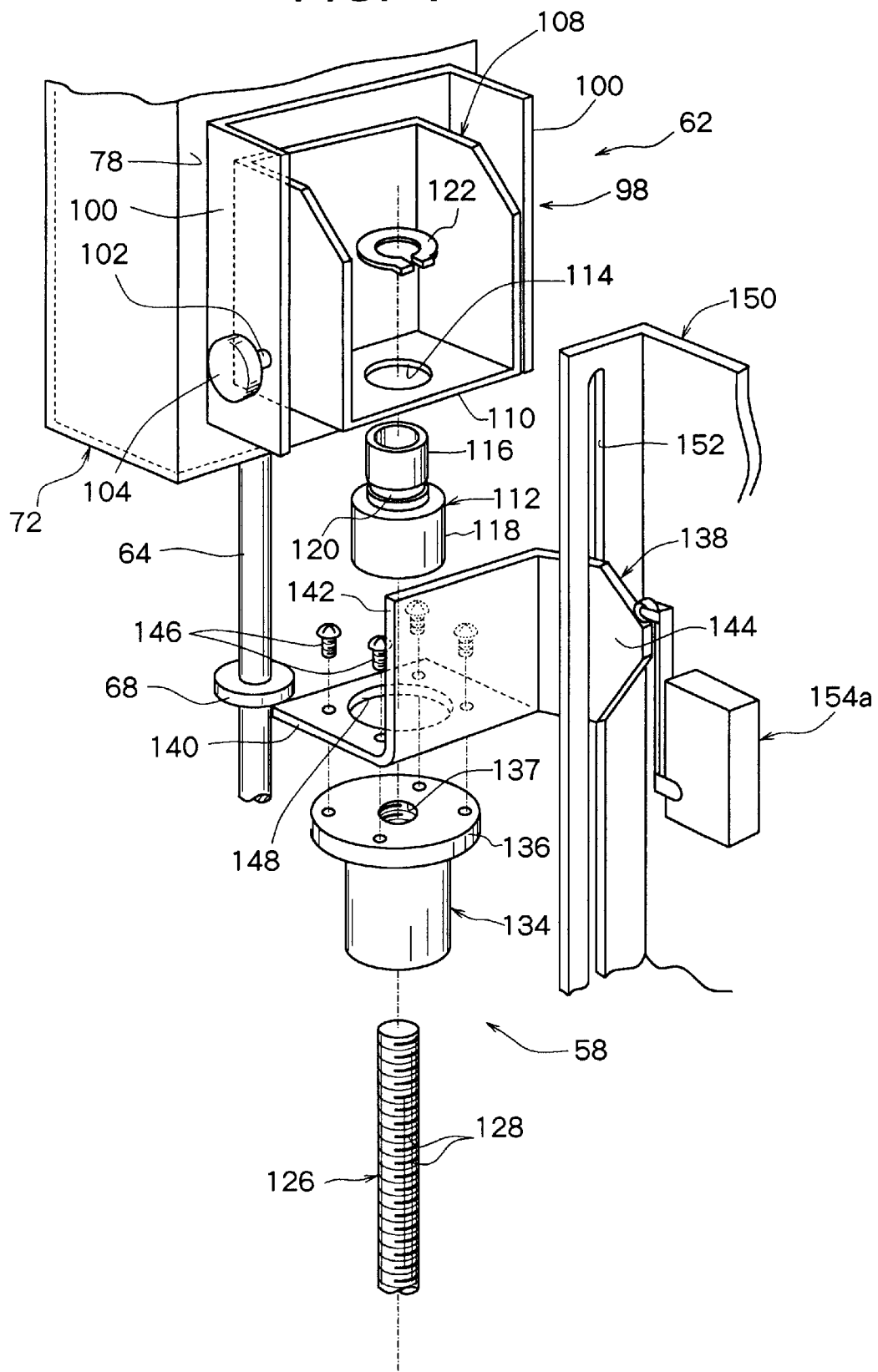
FIG. 7 is an exploded perspective view showing the second weight means and weight supporting means in the pressure molding apparatus of FIG. 1.

Further referring to FIGS. 6 and 7 together with FIG. 1, the second weight means 62 includes a nearly rectangular parallelopipedal casing 72 with an open upper surface and an open front surface, and a cover member 74 to be detachably combined with the casing 72. The casing 72, which may be formed from a suitable metal, has a bottom wall 76, a rear wall 78, and lateral walls 80. The cover member 74, which may similarly be formed from a suitable metal, has an upper wall 82 closing the upper surface of the casing 72, a front wall 86 closing the front surface of the casing 72, an engagingly stopping piece 88 protruding from a rear edge of the upper wall 82, and engagingly stopping pieces 90 protruding from both lateral edges of the upper wall 82 and both lateral edges of the front wall 86. The engagingly stopping piece 88 is engaged with an outer surface of the rear wall 78, and the engagingly stopping pieces 90 are engaged with outer surfaces of both lateral walls 80, whereby the cover member 74 is combined with the casing 72. In a central part of the bottom wall 76 of the casing 72, a circular opening 92 is formed. The rod 64 constituting the first weight means 60 is passed through the opening 92, and entered into the casing 72. The flange 70 fixed to the upper end portion of the rod 64 is positioned in the casing 72. The outer diameter of the flange 70 is larger than the inner diameter of the opening 92, so that the flange 70 cannot move through the opening 92. On the bottom wall 76 of the casing 72, a plurality of weight plates 94 which may be formed from a suitable metal are stacked. The number of the weight plates 94 can be determined by the required weight of the second weight means 62. In a central part of each of the weight plates 94, a circular opening 96 is formed. The outer diameter of the opening 96 is substantially the same as, or somewhat larger than, the outer diameter of the flange 70 fixed to the upper end portion of the rod 64. Thus, the flange 70 can freely move up and down through the openings 96.

Figure 8:
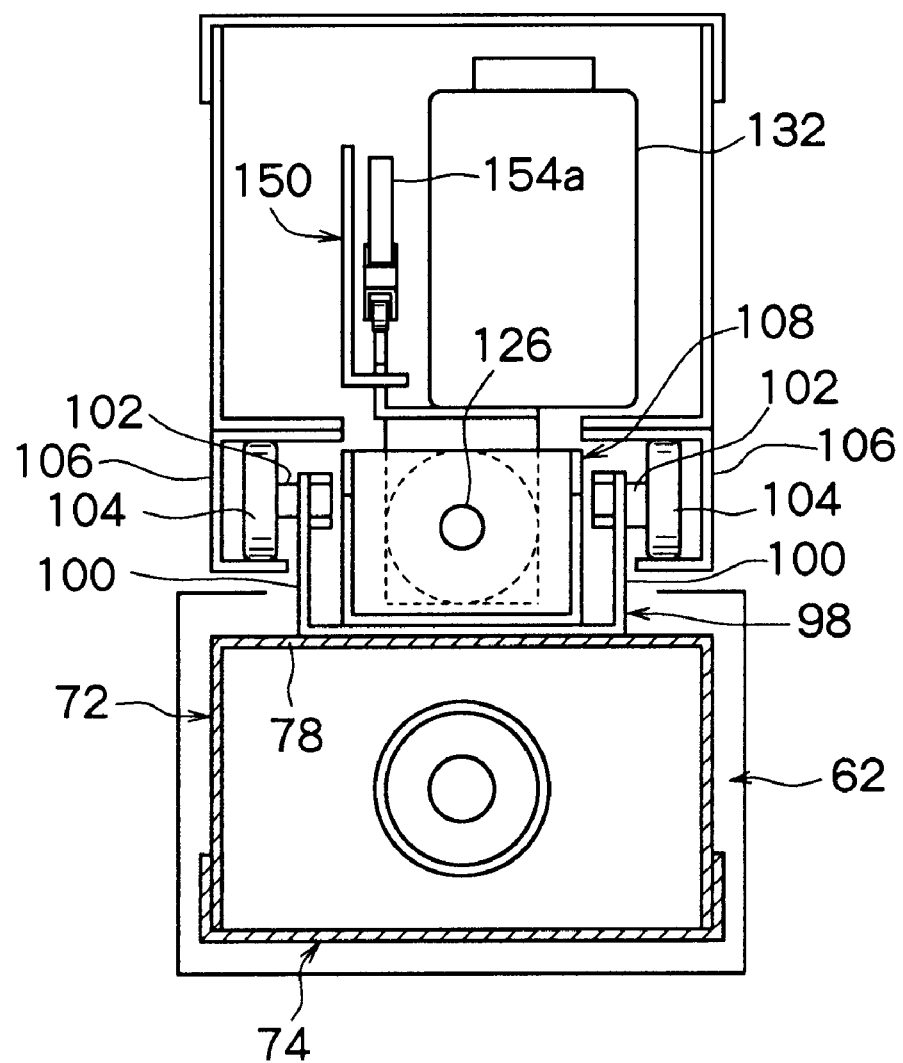
FIG. 8 is a schematic plan view showing the weight means (the first weight means and the second weight means) and the weight supporting means in the pressure molding apparatus of FIG. 1.

With reference to FIG. 7 together with FIG. 1, a metallic channel member 98 extending in an up-and-down direction is fixed to an outer surface of the rear wall 78 of the casing 72 by suitable means such as welding. As shown in FIGS. 7 and 8, a short shaft 102 is fixed to an outside surface of each of side walls 100 of the channel member 98. On each of these short shafts 102, a guided roller 104 is mounted rotatably. As will be easily understood by referring to FIG. 8, a pair of channel-like guide members 106 extending substantially vertically and spaced in a transverse direction (a direction perpendicular to the sheet face in FIG. 1, and a right-and-left direction in FIG. 8) are fixed on the housing 18 of the heating furnace 4. The width between the side walls of the guide member 106 which may be metallic corresponds with the outer diameter of the guided roller 104. Each of the guided rollers 104 is accommodated into each of the pair of guide members 106, whereby the channel member 98, accordingly, the second weight means 62, is mounted so as to be free to move up and down. To the channel member 98, a bracket 108 which may be metallic is fixed by suitable means such as welding. As will be understood by reference to FIG. 9 along with FIG. 7, a supported member 112 is fixed to a bottom wall 110 of the bracket 108. In more detail, a circular opening 114 is formed in the bottom wall 110 of the bracket 108. The supported member 112, which may be metallic, has a cylindrical upper portion 116 of relatively small diameter, and a cylindrical lower portion 118 of relatively large diameter. The outer diameter of the upper portion 116 is substantially the same as the inner diameter of the opening 114, and an annular groove 120 is formed at an outer peripheral surface of the upper portion 116. As clearly illustrated in FIG. 9, the upper portion 116 of the supported member 112 is inserted through the opening 114, and a snap ring 122 is engaged with the annular groove 120 of the upper portion 116, whereby the supported member 112 is fixed to the bottom wall 110 of the bracket 108.

Figure 9:
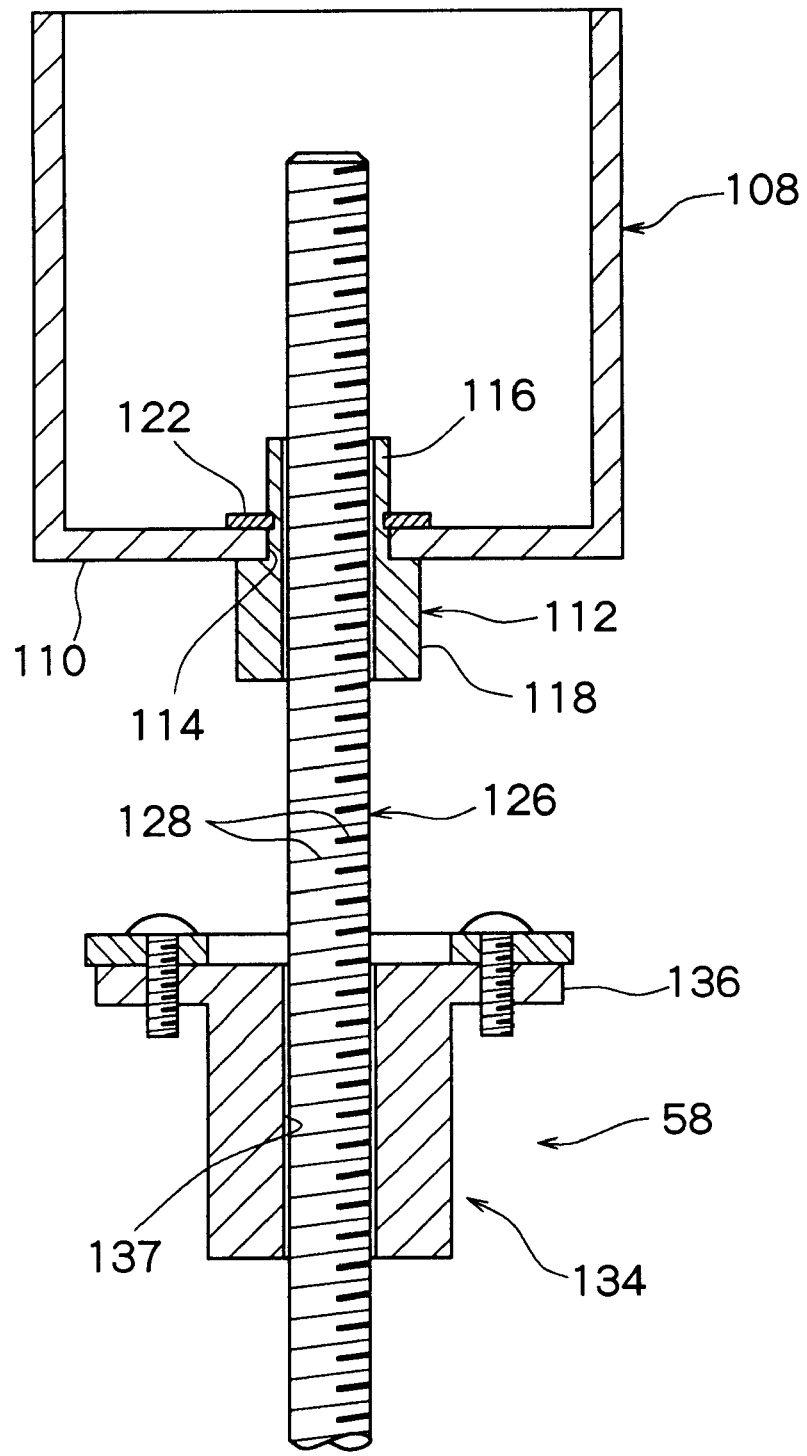
FIG. 9 is a partial sectional view showing the second weight means and part of the weight supporting means in the pressure molding apparatus of FIG. 1.

The weight supporting means 58 will be described by reference to FIGS. 7 to 9 along with FIG. 1. A support block 124 is fixed onto the housing 18 of the heating furnace 4. On the support block 124, a threaded shaft 126 extending substantially vertically upward is mounted rotatably. An external thread 128 is formed at an outer peripheral surface of the threaded shaft 126. As illustrated in FIG. 1, a gear 130 is fixed to a lower end portion of the threaded shaft 126. On the housing 18, an electric motor 132 is mounted. On an output shaft of the motor 132, a rack (not shown) is formed, and engaged with the gear 130. Thus, when the motor 132 is energized, the threaded shaft 126 is rotationally driven via the rack and the gear 130. On the threaded shaft 126, a support member 134 is mounted. The support member 134 is in a cylindrical shape, and has a flange 136 formed at its upper end. In the support member 134, an internally threaded hole 137 (FIG. 9) extending therethrough is formed. This internally threaded hole 137 is screwed on the external thread 128 of the threaded shaft 126. Thus, when the threaded shaft 126 is rotated, the support member 134 is lowered or raised. The supported member 112 fixed to the bracket 108 of the aforementioned second weight means 62 is matched to the support member 134. As will be further mentioned later on, an upper surface of the support member 134 contacts a lower surface of the supported member 112, whereby the weight supporting means 58 supports the second weight means 62 (and also supports the first weight means 60 via the second weight means 62). An inner diameter of the supported member 112, which is in a cylindrical shape, is larger than an outer diameter of the threaded shaft 126, so that the supported member 112 can freely move up and down around the threaded shaft 126.

A detected piece 138 is fixed onto the flange 136 of the support member 134. This detected piece 138 has a connecting portion 140, an upright portion 142 extending upward from a rear edge of the connecting portion 140, and a detected portion 144 extending rearward from the upright portion 142. The connecting portion 140 is fixed to the flange 136 by four bolts 146. At a center of the connecting portion 140, a circular opening 148 is formed. An inner diameter of this opening 148 is somewhat larger than an outer diameter of a lower portion of the supported member 112. Thus, the upper surface of the support member 134 is directly contacted with the lower surface of the supported member 112. As will be understood by referring to FIG. 9 along with FIG. 7, a frame member 150 extending substantially vertically upward is disposed on the housing 18 of the heating furnace 4. In the frame member 150, an elongated slit 152 extending in a vertical direction is formed. The detected portion 144 of the detected piece 138 is protruded rearward through the slit 152. On the frame member 150, three detectors 154a, 154b and 154c are mounted with spacing in an up-and-down direction. These detectors 154a, 154b and 154c can each be composed of a microswitch. As will be further mentioned later on, when the support member 134 is raised to an uppermost position indicated by a solid line in FIG. 1, the detector 154a detects the detected piece 138. When the support member 134 is lowered to a position slightly beyond a low load imposed position indicated by a two-dot chain line 134b in FIG. 1, the detector 154b detects the detected piece 138. When the support member 134 is lowered to a position slightly beyond a high load imposed position indicated by a two-dot chain line 134c in FIG. 1, the detector 154c detects the detected piece 138.

Mainly referring to FIG. 1, a typical example of the manner of molding by the above-described pressure molding apparatus will be explained in summary. Prior to the initiation of molding, the heating means 22 of the heating furnace 4 is energized to preheat the interior of the heating furnace 4 to, say, 900° C. The door 20 of the heating furnace 4 is opened, and the mold assembly 28, in which the raw material 40 to be molded has been charged into the mold body 30, and the pressure piston 32 has been partly inserted, as shown in FIG. 2(a), is laid on the furnace floor plate 26 of the heating space 6. Then, the door 20 is closed, and a molding start switch (not shown) is operated to start molding. During molding, the heating space 6 inside the heating furnace 4 is maintained at, say, 900° C.

At the start of molding, the support member 134 of the weight supporting means 58 is located at the uppermost position indicated by the solid line in FIG. 1, and the detector 154a detects the detected piece 138. In this state, the support member 134 of the weight supporting means 58 contacts the supported member 112 of the second weight means 62 to support the second weight means 62. Furthermore, the flange 70 fixed to the upper end portion of the rod 64 in the first weight means 60 is supported on the bottom wall 76 of the casing 72 of the second weight means 62. Thus, the first weight means 60 is also supported by the weight supporting means 58 via the second weight means 62. As shown by a solid line in FIG. 1, the lower end of the rod 64 in the first weight means 60 is positioned apart in an upward direction from the pressure piston 32 of the mold assembly 28, so that no load is imposed on the pressure piston 32.

When the molding start switch is operated in the foregoing manner, normal rotation of the motor 132 of the weight supporting means 58 is started, whereby the support member 134 is gradually lowered. Accordingly, the second weight means 62 and the first weight means 60 are also gradually lowered. When the support member 134 is lowered to the position indicated by the two-dot chain line 134b in FIG. 1, i.e., the position of starting low load imposition, the lower end of the rod 64 in the first weight means 60 contacts an upper end of the pressure piston 32 in the mold assembly 28, as shown by a two-dot chain line 64b in FIG. 1, so that the lowering of the first weight means 60 is inhibited. When the support member 134 is further lowered, slightly, beyond the position of starting low load imposition, the flange 70 fixed to the upper end portion of the rod 64 in the first weight means 60 is separated upward from the bottom wall 76 of the casing 72 in the second weight means 62. As a result, suspension of the first weight means 60 by the second weight means 62 is released. Thus, the load of the first weight means 60 is imposed on the pressure piston 32 of the mold assembly 28 to put a low load on the raw material 40 to be molded, thereby initiating its molding. At the same time, the detector 154b detects the detected piece 138, thereby stopping the motor 132. Hence, a low load imposed state is continued.

When a predetermined time, e.g., about 10 to 15 minutes, elapses after detection of the detected piece 138 by the detector 154b, normal rotation of the motor 132 is resumed. Thus, the support member 134 and the second weight means 62 supported thereby begin to descend again. When the support member 134 is lowered to a position of high load imposition indicated by a two-dot chain line 134c in FIG. 1, the bottom wall 76 of the casing 72 in the second weight means 62 contacts the flange 68 fixed to a nearly middle part of the rod 64 in the first weight means 60, as shown by two-dot chain lines 68c and 76c in FIG. 1. Thus, the lowering of the second weight means 62 is inhibited. When the support member 134 is further lowered, slightly, beyond the position of starting high load imposition, the supported member 112 in the second weight means 62 is separated upward from the support member 134. As a result, suspension of the second weight means 62 by the weight supporting means 58 is released. Thus, the load of the second weight means 62 is imposed on the pressure piston 32 of the mold assembly 28 via the first weight means 60 to increase the load on the raw material 40, which is to be molded, from a low load to a high load. At the same time, the detector 154c detects the detected piece 138, thereby stopping the motor 132. Hence, a high load imposed state is continued.

When a predetermined time, e.g., about 30 to 40 minutes, elapses after detection of the detected piece 138 by the detector 154c, reverse rotation of the motor 132 is started to raise the support member 134 gradually. When the support member 134 is raised past the high load imposition start position indicated by the two-dot chain line 134c in FIG. 1, the support member 134 contacts the supported member 112 to support it. Thus, the load of the second weight means 62 is removed from the pressure piston 32 of the mold assembly 28. When the support member 134 is raised past the low load imposition start position indicated by the two-dot chain line 134b in FIG. 1, the bottom wall 76 of the casing 72 in the second weight means 62 contacts the flange 70 fixed to the upper end portion of the rod 64 in the first weight means 60 to support the flange 70. Thus, the load of the first weight means 60 is also removed from the pressure piston 32 of the mold assembly 28. When the support member 134 is raised to the highest position indicated by the solid line in FIG. 1, the detector 154a detects the detected piece 138, whereupon the motor 132 is stopped.

When a predetermined time, e.g., about 45 to 60 minutes, elapses after initiation of reverse rotation of the motor 132 in the foregoing manner, the heating means 22 in the heating furnace 4 is deenergized. Moreover, a suitable alarm (not shown) is energized to inform an operator of the completion of the molding process. The operator opens the door 20, and withdraws from the heating furnace 4 the mold assembly 28 containing a molded dental crown 42. During the period from the removal of load from the pressure piston 32 of the mold assembly 28 until the door 20 is opened and the mold assembly 28 withdrawn from the heating furnace 4, the temperature inside the heating furnace 4 can be lowered to a predetermined temperature, if desired.

In the above-described pressure molding apparatus 2, a low load is imposed on the pressure piston 32 of the mold assembly 28, and then, after a lapse of a predetermined time, a high load is imposed thereon. If desired, a required high load can be imposed from the start of load imposition. According to the inventors' experience, however, imposing the required high load from the start of load imposition tends to form flow mark on the molded dental crown 42.

Figure 10:
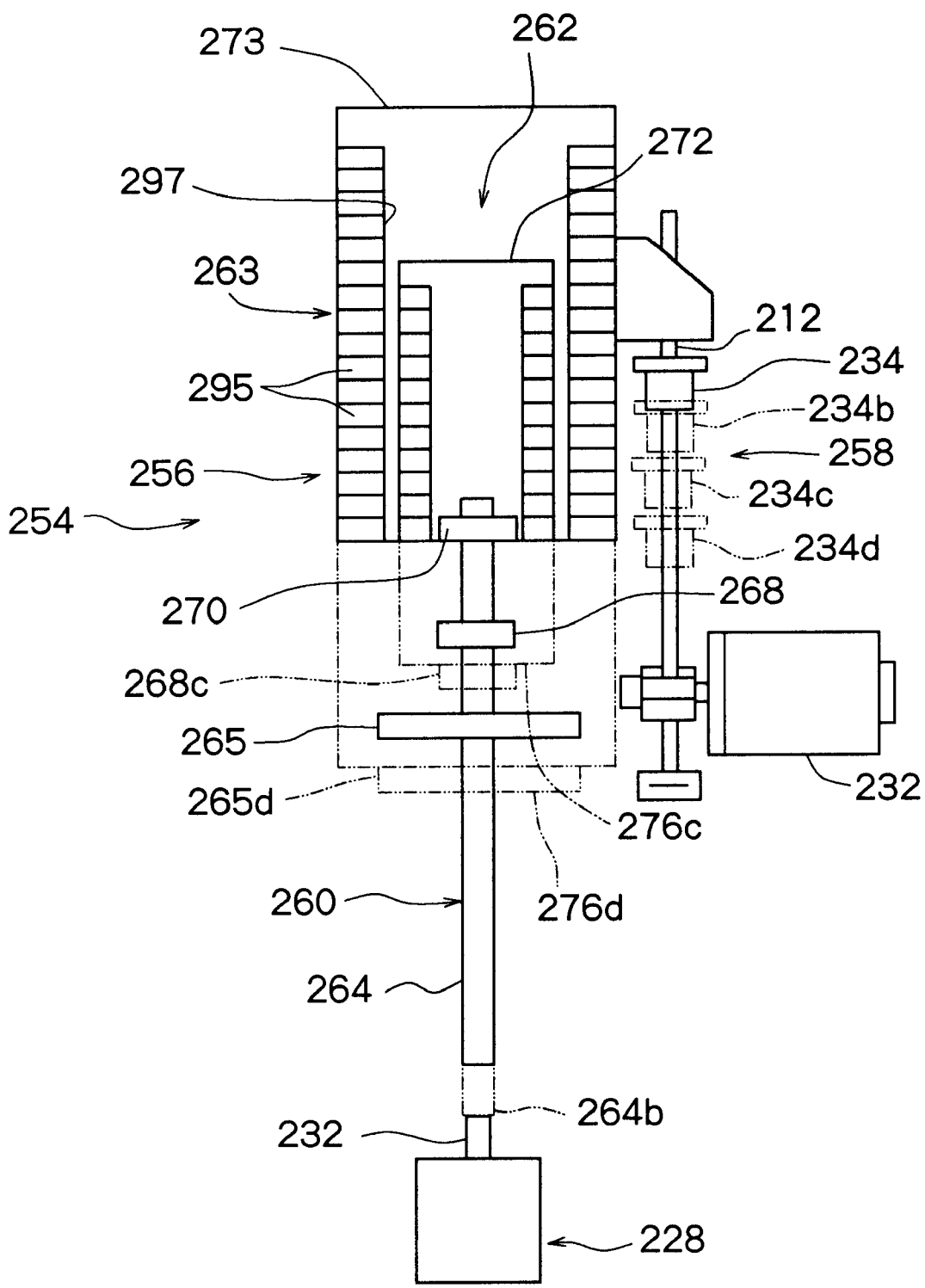
FIG. 10 is a schematic sectional view showing a modification of load imposing means (the weight means and the weight supporting means).

If desired, the load to be imposed may be gradually increased in 3 or 4 or more steps. FIG. 10 illustrates a modification of the load imposing means constituted so as to increase the load in 3 steps. In load imposing means 254 shown in FIG. 10, weight means 256 is composed of first weight means 260, second weight means 262, and third weight means 263. Weight supporting means 258 is provided on and along the third weight means 263 to support the third weight means 263 directly, support the second weight means 262 via the third weight means 263, and support the first weight means 260 via the third weight means 263 and the second weight means 262. With reference to FIG. 10, the first weight means 260 is substantially the same as the first weight means 60 in the aforementioned pressure molding apparatus 2, except that a relatively large, circular flange 265 is added to an intermediate portion of a rod 264. The second weight means 262 is substantially the same as the second weight means 62 in the aforementioned pressure molding apparatus 2, except that there is no member provided on and along an outer surface of a rear wall of a casing 272, and that the casing 272 is housed in a casing 273 of the third weight means 263. The third weight means 263 has the casing 273 of a relatively large size housing the casing 272 of the second weight means 262. In a bottom wall of this casing 273, a somewhat smaller opening than a cross sectional shape of the casing 272 of the second weight means 262 is formed. Inside the casing 273, a plurality of weight plates 295 are housed. In a central part of each of the weight plates 295, a rectangular opening 297 slightly larger than the cross sectional shape of the casing 272 in the second weight means 262 is formed. The casing 272 of the second weight means 262 can freely move up and down through the openings 297. On and along a rear wall of the casing 273 in the third weight means 263, there is provided substantially the same constituent element as the constituent element provided on and along the rear wall 78 of the casing 72 of the second weight means 62 in the aforementioned pressure molding apparatus 2. This constituent element can be supported by the weight supporting means 258. The constitution of the weight supporting means 258 may be substantially the same as the constitution of the weight supporting means 58 in the aforementioned pressure molding apparatus 2, except that the support member 234 is detected at four positions, i.e., an uppermost position, a low load imposition start position, a medium load imposition start position, and a high load imposition start position.

In the load imposing means 254 shown in FIG. 10, at the start of molding, the support member 234 of the weight supporting means 258 is located at the uppermost position indicated by a solid line in FIG. 10. In this state, the support member 234 of the weight supporting means 258 contacts a supported member 212 of the third weight means 263 to support the third weight means 263. Also, the casing 272 of the second weight means 262 is supported on a bottom wall of the casing 273 of the third weight means 263. Thus, the second weight means 262 is supported by the weight supporting means 258 via the third weight means 263. Furthermore, a flange 270 fixed to an upper end portion of a rod 264 in the first weight means 260 is supported on the bottom wall of the casing 272 of the second weight means 262. Thus, the first weight means 260 is also supported by the weight supporting means 258 via the third weight means 263 and the second weight means 262. As shown by a solid line in FIG. 10, a lower end of the rod 264 in the first weight means 260 is positioned apart in an upward direction from a pressure piston 232 of a mold assembly 228, so that no load is imposed on the pressure piston 232.

When a molding start switch is operated, normal rotation of a motor 132 of the weight supporting means 258 is started, whereby the support member 234 is gradually lowered. Accordingly, the third weight means 263, the second weight means 262 and the first weight means 260 are also gradually lowered. When the support member 234 is lowered to a position indicated by a two-dot chain line 234b in FIG. 10, i.e., the position of starting low load imposition, the lower end of the rod 264 in the first weight means 260 contacts an upper end of the pressure piston 232 in the mold assembly 228, as shown by a two-dot chain line 264b in FIG. 10. Thus, the lowering of the first weight means 260 is inhibited. When the support member 234 is further lowered, slightly, beyond the position of starting low load imposition, the flange 270 fixed to the upper end portion of the rod 264 in the first weight means 260 is separated upward from the bottom wall of the casing 272 in the second weight means 262. As a result, suspension of the first weight means 260 by the second weight means 262 is released. Thus, the load of the first weight means 260 is imposed on the pressure piston 232 of the mold assembly 228.

When the support member 234, and the third weight means 263 and second weight means 262 supported thereby are lowered further, whereby the support member 234 is lowered to the position of medium load imposition indicated by a two-dot chain line 234c in FIG. 10, the bottom wall of the casing 272 in the second weight means 262 contacts a flange 268 fixed to a nearly middle part of the rod 264 in the first weight means 260, as shown by two-dot chain lines 268c and 276c in FIG. 10. Thus, the lowering of the second weight means 262 is inhibited. When the support member 234 is further lowered, slightly, beyond the position of starting medium load imposition, the casing 272 in the second weight means 262 is separated upward from the bottom wall of the casing 273 in the third weight means 263. As a result, support of the second weight means 262 by the third weight means 263 is released. Thus, the load of the second weight means 262 is imposed on the pressure piston 232 of the mold assembly 228 via the first weight means 260 to increase the imposed load from a low load to a medium load.

When the support member 234, and the third weight means 263 supported thereby are lowered further, whereby the support member 234 is lowered to a position of high load imposition indicated by a two-dot chain line 234d in FIG. 10, the bottom wall of the casing 273 in the third weight means 263 contacts a flange 265 fixed to a nearly middle part of the rod 264 in the first weight means 260, as shown by two-dot chain lines 265d and 276d in FIG. 10. Thus, the lowering of the third weight means 263 is inhibited. When the support member 234 is further lowered, slightly, beyond the position of starting high load imposition, the supported member 212 in the third weight means 263 is separated upward from the support member 234. As a result, support of the third weight means 263 by the weight supporting means 258 is released. Thus, the load of the third weight means 263 is also imposed on the pressure piston 232 of the mold assembly 228 via the first weight means 260 to increase the imposed load from the medium load to a high load.

The preferred embodiments of the pressure molding apparatus constituted in accordance with the present invention have been described in detail above by reference to the accompanying drawings. However, it should be understood that the present invention is not limited to these embodiments, and various changes and modifications may be made without departing from the spirit and scope of the invention.

What we claim is:

1. A non-pneumatic pressure molding apparatus comprising:

a furnace defining a heating space for accommodating a mold assembly including a mold body charged with a raw material to be molded, and a pressure piston for pressurizing the raw material;

heating means for heating the heating space; and load imposing means for imposing a load on the pressure piston to mold the raw material, wherein the load imposing means includes at least one weight means and weight supporting means, and the weight supporting means is selectively set in a load-free state in which the weight supporting means supports the weight means so that the weight of the weight means is not imposed on the pressure piston, and a load imposed state in which the weight supporting means releases the support of the weight means so that the weight of the weight means is imposed on the pressure piston.

2. The pressure molding apparatus of claim 1, wherein the load imposing means includes first weight means and second weight means, and the weight supporting means is selectively set in the load-free state in which the weight supporting means supports both the first weight means and the second weight means so that none of the weights of the first weight means and the second weight means are imposed on the pressure piston, a low load imposed state in which the weight supporting means releases the support of the first weight means so that the weight of the first weight means is imposed on the pressure piston, and a high load imposed state in which the weight supporting means releases the support of both the first weight means and the second weight means so that the weights of the first and second weight means are imposed on the pressure piston.

3. The pressure molding apparatus of claim 2, wherein the furnace has a floor wall defining a lower surface of the heating space, and a ceiling wall defining an upper surface of the heating space; the mold assembly is laid on the floor wall; the pressure piston is stretched outward upwardly from the mold body;

the first weight means is placed above the pressure piston and stretched through the ceiling wall; the second weight means is placed above the first weight means; the weight supporting means includes a supporting member, and hoisting and lowering means for hoisting and lowering the supporting member; when the supporting member is brought to a hoisted position, the second weight means supports the first weight means, and the supporting member supports the second weight means, and supports the first weight means via the second weight means; when the supporting member is lowered beyond a low load imposed position, the first weight means contacts the pressure piston, so that the support of the first weight means by the second weight means is released, whereby the load of the first weight means is imposed on the pressure piston; when the supporting member is further lowered beyond a high load imposed position, the second weight means contacts the first weight means, so that the support of the second weight means by the supporting member is released, whereby the load of the first weight means is imposed on the pressure piston, and the load of the second weight means is also imposed on the pressure piston via the first weight means.

4. The pressure molding apparatus of claim 3, wherein the second weight means includes a bracket member having an opening formed in a bottom wall; the first weight means includes a rod extending in an up-and-down direction through the opening; an engagingly stopping flange positioned above the bottom wall of the bracket member, and a contact flange positioned below the bottom wall of the bracket member are disposed on the rod; the bottom wall of the bracket member supports the engagingly stopping flange, whereby the second weight means supports the first weight means; and the bottom wall of the bracket member contacts the contact flange, whereby the load of the second weight means is imposed on the pressure piston via the first weight means.

5. The pressure molding apparatus of claim 3, wherein a contact member is disposed on the bracket member, and the weight supporting member supports the second weight means by contacting a lower surface of the contact member.

6. The pressure molding apparatus of claim 1, wherein the furnace includes a floor wall defining a lower surface of the heating space, and a furnace floor plate removably mounted on the floor wall, and position regulating means for regulating the position of the mold assembly to be placed on an upper surface of the furnace floor plate is disposed on the upper surface of the furnace floor plate.

* * * * *